US007511149B2

(12) United States Patent
Arndt et al.

(10) Patent No.: US 7,511,149 B2
(45) Date of Patent: Mar. 31, 2009

(54) PROCESS FOR THE OXIDATION OF CERTAIN SUBSTITUTED SULFILIMINES TO INSECTICIDAL SULFOXIMINES

(75) Inventors: Kim E. Arndt, Carmel, IN (US); Douglas C. Bland, Midland, MI (US); David E. Podhorez, Midland, MI (US); James R. McConnell, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 56 days.

(21) Appl. No.: 11/704,756

(22) Filed: Feb. 9, 2007

(65) Prior Publication Data
US 2008/0194634 A1  Aug. 14, 2008

(51) Int. Cl.
| | |
|---|---|
| C07D 237/12 | (2006.01) |
| C07D 237/14 | (2006.01) |
| C07D 237/16 | (2006.01) |
| C07D 237/18 | (2006.01) |
| C07D 237/20 | (2006.01) |
| C07D 239/26 | (2006.01) |
| C07D 239/30 | (2006.01) |
| C07D 239/32 | (2006.01) |
| C07D 241/10 | (2006.01) |
| C07D 241/12 | (2006.01) |
| C07D 241/16 | (2006.01) |
| C07D 241/18 | (2006.01) |
| C07D 241/20 | (2006.01) |
| C07D 213/61 | (2006.01) |
| C07D 213/62 | (2006.01) |
| C07D 213/72 | (2006.01) |
| C07D 213/89 | (2006.01) |
| C07D 277/24 | (2006.01) |
| C07D 277/34 | (2006.01) |
| C07D 277/36 | (2006.01) |
| C07D 277/50 | (2006.01) |
| C07D 285/08 | (2006.01) |
| C07D 275/02 | (2006.01) |
| C07D 275/03 | (2006.01) |
| C07D 263/32 | (2006.01) |
| C07D 263/34 | (2006.01) |
| C07D 263/36 | (2006.01) |
| C07D 263/46 | (2006.01) |
| C07D 271/06 | (2006.01) |
| C07D 271/07 | (2006.01) |
| C07D 271/10 | (2006.01) |
| C07D 271/113 | (2006.01) |
| C07D 261/06 | (2006.01) |
| C07D 261/08 | (2006.01) |
| C07D 261/12 | (2006.01) |
| C07F 213/16 | (2006.01) |
| C07F 261/10 | (2006.01) |

(52) U.S. Cl. ............... 546/281.4; 544/224; 544/241; 544/315; 544/318; 544/334; 544/406; 544/408; 544/409; 546/287; 546/288; 546/286; 546/327; 546/339; 546/345; 546/311; 548/183; 548/201; 548/205; 548/203; 548/202; 548/128; 548/129; 548/130; 548/136; 548/142; 548/206; 548/213; 548/226; 548/225; 548/235; 548/236; 548/131; 548/132; 548/143; 548/144; 548/243; 548/247; 548/248; 548/318.5; 548/317.1; 548/322.5; 548/323.5; 548/334.5; 548/341.1; 548/342.1; 548/343.1; 548/263.4; 548/263.8; 548/366.4; 548/367.1; 548/369.1; 548/370.4; 548/374.1; 548/376.1; 548/373.1

(58) Field of Classification Search ............... 544/224, 544/241, 315, 318, 334, 406, 408, 409; 546/287, 546/288, 286, 327, 339, 345, 281.4; 548/183, 548/201, 205, 203, 202, 128, 129, 130, 136, 548/142, 206, 213, 226, 225, 235, 236, 131, 548/132, 143, 144, 243, 247, 248, 218.5, 548/317.1, 322.5, 323.5, 334.5, 341.1, 342.1, 548/343.1, 263.4, 366.4, 367.1, 369.1, 370.4, 548/374.1, 376.1, 373.1
See application file for complete search history.

(56) References Cited

U.S. PATENT DOCUMENTS
2005/0228027 A1  10/2005  Zhu et al.

FOREIGN PATENT DOCUMENTS
| | | |
|---|---|---|
| GB | 1307271 | 2/1973 |
| JP | 53009717 | 1/1978 |

OTHER PUBLICATIONS

U.S. Appl. No. 11/704,397, filed Feb. 9, 2007, Jim X. Huang, et al.
U.S. Appl. No. 11/704,759, filed Feb. 9, 2007, Stephen T. Heller, et al.
U.S. Appl. No. 11/704,796, filed Feb. 9, 2007, Kevin G. Meyer, et al.
U.S. Appl. No. 11/704,797, filed Feb. 9, 2007, Michael R. Loso, et al.
U.S. Appl. No. 11/704,820, filed Feb. 9, 2007, Yuanming Zhu, et al.
U.S. Appl. No. 11/704,824, filed Feb. 9, 2007, Jim X. Huang, et al.
U.S. Appl. No. 11/704,825, filed Feb. 9, 2007, James M. Renga, et al.
U.S. Appl. No. 11/704,842, filed Feb. 9, 2007, Michael R. Loso, et al.
U.S. Appl. No. 11/704,853, filed Feb. 9, 2007, Michael R. Loso, et al.
U.S. Appl. No. 11/705,185, filed Feb. 9, 2007, Michael R. Loso, et al.
Shimizu, Hiroshi, et al. Synthesis and Properties of a Novel Cyclic Sulfilimine, 2-Methyl-2,4-1-benzodithiazin-2-ium-1-ide; Heteroatom Chemistry, vol. 6, No. 2, 1995, pp. 167-176.
Shitov, O.P., et al. "Synthesis of novel types of organosulfur nitro compounds" [Bibliographic Information only]; Izvestiya Akadmii Nauk SSSR, Seriya Khimicheskaya, 1237-8. CODEN: IASKA6; ISSN: 0002-3353. AN 1991:49 CAPLUS.
Veale, Harry S., et al. "New Method of Preparation of Acyl- and Sulfonylsulfoximines: Ruthenium Tetroxide Oxidation Of Sulfilimines;" Tetrahedron Letters No. 6, Pergamon Press, Great Britain, 1978, pp. 503-506.
International Search Report for PCT/US2007/003783.
Written Opinion of the International Search Authority for PCT/US2007/003783.

*Primary Examiner*—Mark L Berch
*Assistant Examiner*—Cecilia M Jaisle
(74) *Attorney, Agent, or Firm*—Carl Corvin

(57) ABSTRACT

Insecticidal sulfoximines are produced efficiently and in high yield by the oxidation of the corresponding sulfilimine with ruthenium tetroxide or an alkali metal permanganate.

12 Claims, No Drawings

PROCESS FOR THE OXIDATION OF CERTAIN SUBSTITUTED SULFILIMINES TO INSECTICIDAL SULFOXIMINES

BACKGROUND OF THE INVENTION

The present invention concerns a process for preparing insecticidal sulfoximines from certain substituted sulfilimines.

The substituted sulfilimines are useful intermediates for the preparation of certain new insecticides; see, for example, U.S. Patent Publication 2005/0228027. It would be advantageous to produce insecticidal sulfoximines efficiently and in high yield from the corresponding sulfilimines.

SUMMARY OF THE INVENTION

The present invention concerns a process for the oxidation of certain substituted sulfilimines, having the general structure of (I),

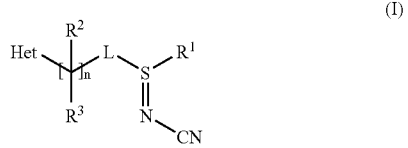

wherein
Het represents:

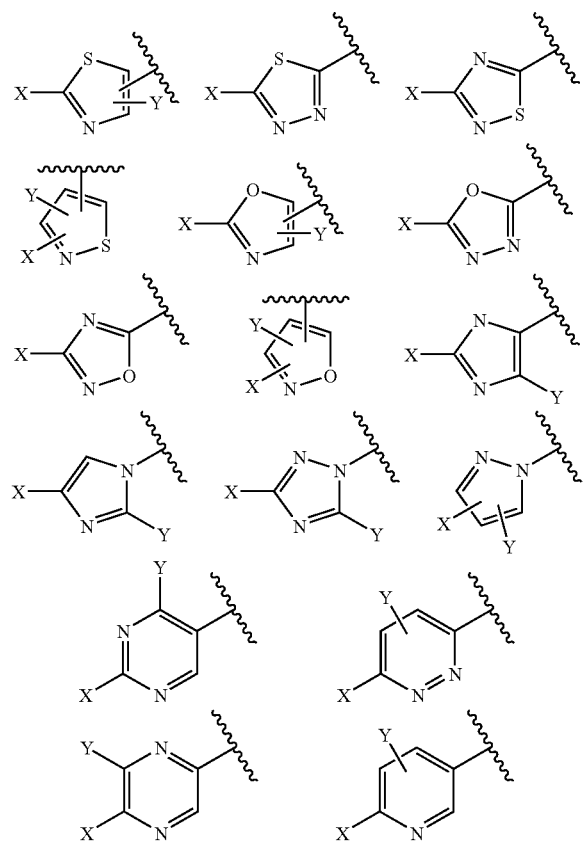

X represents halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $SO_mR^6$ where m is an integer from 0-2, $COOR^4$ or $CONR^4R^5$;

Y represents hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $SO_mR^1$ where m is an integer from 0-2, $COOR^4$, $CONR^4R^5$, aryl or heteroaryl;

n is an integer from 0-3;

L represents either a single bond, —CH(CH$_2$)$_p$— where $R^1$, S and L taken together represent a 4-, 5-, or 6-membered ring and p is an integer from 1-3, —CH(CH$_2$OCH$_2$)— where $R^1$, S and L taken together represent a 6-membered ring, or —CH— where L, $R^2$ and the common carbon to which they connect taken together represent a 4-, 5-, or 6-membered ring with up to, but no more than, 1 heteroatom.

$R^1$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl, heteroarylalkyl, or —CH$_2$— in cases where $R^1$, S and L taken together represent a 4-, 5-, or 6-membered ring;

$R^2$ and $R^3$ independently represent hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $SO_mR^6$ where m is an integer from 0-2, $COOR^4$, $CONR^4R^5$, arylalkyl, heteroarylalkyl, or $R^2$ and $R^3$ and the common carbon to which they attach form a 3-6 membered ring;

$R^4$ and $R^5$ independently represent hydrogen, $C_1$-$C_4$ alkyl, $C_1$-$C_4$ haloalkyl; $C_3$-$C_6$ alkenyl, $C_3$-$C_6$ alkynyl, $C_3$-$C_6$ haloalkenyl, aryl, heteroaryl, arylalkyl or heteroarylalkyl; and $R^6$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl or heteroarylalkyl;

to form insecticidal sulfoximines having the structure (Ia):

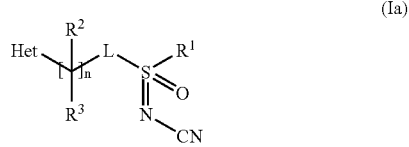

wherein $R^1$, $R^2$, $R^3$, Het, L and n are as previously defined. In the process, the sulfilimine of formula I is oxidized to the corresponding sulfoximine of formula Ia by contacting the sulfilimine in a suitable organic solvent that is essentially inert to the strong oxidizing conditions with an oxidizing agent comprising ruthenium tetraoxide or an alkali metal permanganate at a temperature from about −10 to about 45° C.

The process is well suited to oxidize sulfilimines of the following classes:

(1) Compounds of formula (I) wherein Het is (6-substituted)pyridin-3-yl or (2-substituted)thiazol-5-yl and where X is halogen or $C_1$-$C_2$ haloalkyl and Y is hydrogen (2) Compounds of formula (I) wherein $R^2$ and $R^3$ are as previously defined, $R^1$ is methyl, n is 1, and L is a single bond, having the structure:

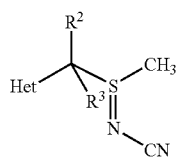

(3) Compounds of formula (I) wherein n is 1, $R^1$, S and L taken together form a standard 4-, 5-, or 6-membered ring such that L is —CH(CH$_2$)$_p$— and p is an integer from 1-3, and $R^1$ is —CH$_2$— having the structure:

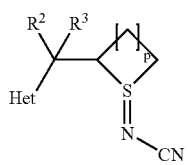

(4) Compounds of formula (I) wherein n is 0, $R^1$, S and L taken together form a standard 4-, 5-, or 6-membered ring such that L is —CH(CH$_2$)$_p$— and p is an integer from 1-3, and $R^1$ is —CH$_2$— having the structure:

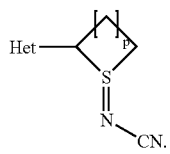

DETAILED DESCRIPTION OF THE INVENTION

Throughout this document, all temperatures are given in degrees Celsius, and all percentages are weight percentages unless otherwise stated.

The terms "alkyl", "alkenyl" and "alkynyl", as well as derivative terms such as "alkoxy", "acyl", "alkylthio", "arylalkyl", "heteroarylalkyl" and "alkylsulfonyl", as used herein, include within their scope straight chain, branched chain and cyclic moieties. Thus, typical alkyl groups are methyl, ethyl, 1-methyl-ethyl, propyl, 1,1-dimethylethyl, and cyclopropyl. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The term "haloalkyl" and "haloalkenyl" includes alkyl and alkenyl groups substituted with from one to the maximum possible number of halogen atoms, all combinations of halogens included. The term "halogen" or "halo" includes fluorine, chlorine, bromine and iodine, with fluorine being preferred. The terms "alkenyl" and "alkynyl" are intended to include one or more unsaturated bonds.

The term "aryl" refers to a phenyl, indanyl or naphthyl group. The term "heteroaryl" refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$ OC(O)alkyl, $C_1$-$C_6$ NHC(O)alkyl, C(O)OH, $C_1$-$C_6$C(O)Oalkyl, C(O)NH$_2$, $C_1$-$C_6$C(O)NHalkyl, or $C_1$-$C_6$C(O)N(alkyl)$_2$, provided that the substituents are sterically compatible and the rules of chemical bonding and strain energy are satisfied.

The sulfilimine starting materials of Formula I are the subject matter of a patent application filed concurrently with this application and certain of them have been disclosed in U.S. Patent Publication 2005/0228027. They can be prepared from the corresponding sulfides according to the following Schemes A and B.

The compounds of formula (I), wherein $R^1$, $R^2$, $R^3$, n, and L are as previously defined can be prepared by the methods illustrated in Scheme A.

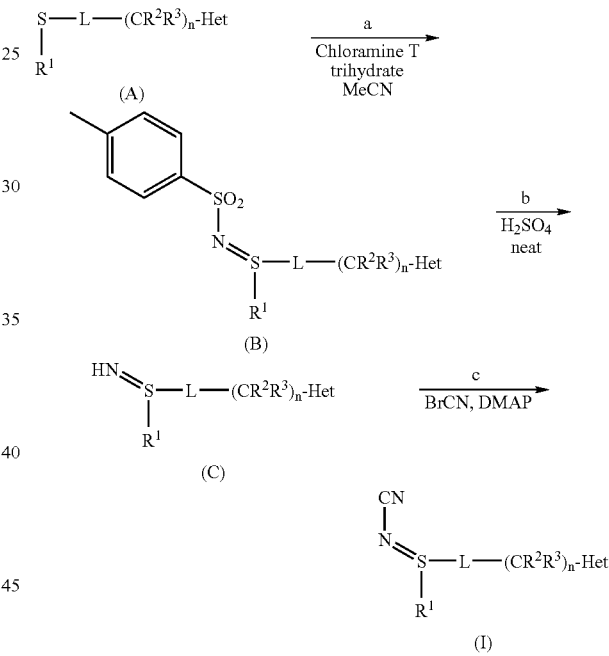

Scheme A

In step a of Scheme A, sulfide of formula (A) is iminated with chloramine T trihydrate a polar solvent at 25-60° C. to provide an N-tosylsulfilimine of formula (B). In most cases, acetonitrile is the preferred solvent for the imination.

In step b of Scheme A, N-tosylsulfilimine (B) is hydrolyzed in neat sulfuric acid to provide the N-unsubstituted sulfilimine (C). This product is typically used directly in the next reaction without further purification.

In step c of Scheme A, the nitrogen of sulfilimine (C) can be cyanated with cyanogen bromide in the presence of a base to provide N-substituted sulfilimine (I).

The compounds of formula (Ia), wherein Het, $R^1$, $R^2$, $R^3$, n, and L are as previously defined can be prepared by the method illustrated in Scheme B. Accordingly, the precursor sulfide is oxidized with iodobenzene diacetate in the presence of cyanamide at 0° C. to give sulfilimine (Ia). The reaction can be carried out in a polar aprotic solvent like CH$_2$Cl$_2$.

Scheme B

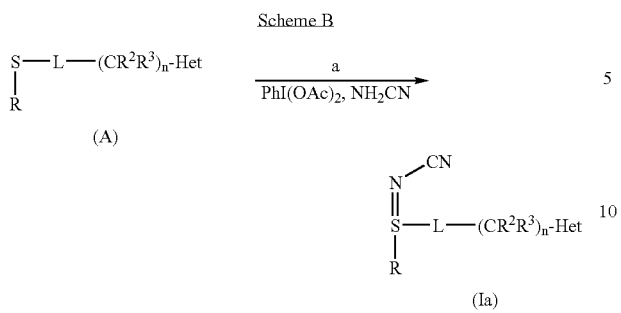

The precursor sulfides (A) can, in turn, be prepared in different ways as illustrated in Schemes C, D, E, F, G, H and I.

In Scheme C, the sulfide of formula ($A_1$), wherein L is a single bond, n is 1, $R^3$=H, and $R^1$, $R^2$ and Het are as previously defined can be prepared from halides of formula (D) by nucleophilic substitution with the sodium salt of an alkyl thiol.

Scheme C

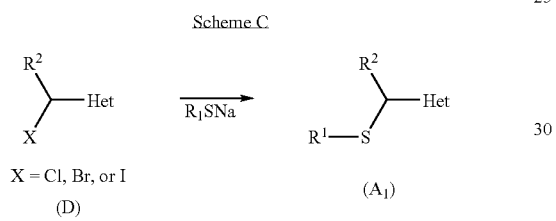

In Scheme D, the sulfide of formula ($A_2$), wherein L is a single bond, n is 3, $R^3$=H, and $R^1$, $R^2$ and Het are as previously defined, can be prepared from the chloride of formula (E) by reacting with a 2-mono substituted methyl malonate in the presence of base such as potassium tert-butoxide to provide 2,2-disubstitued malonate, hydrolysis under basic conditions to form a diacid, decarboxylation of the diacid by heating to give a monoacid, reduction of the monoacid with borane-tetrahyrofuran complex to provide an alcohol, tosylation of the alcohol with toluenesulfonyl chloride (tosyl chloride) in the presence of a base like pyridine to give a tosylate and replacement of the tosylate with the sodium salt of the desired thiol.

Scheme D

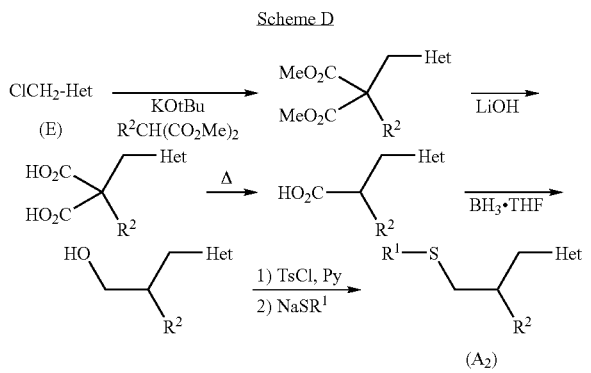

In Scheme E, the sulfide of formula ($A_3$), wherein L is a single bond, n is 2, $R^3$=H, and $R^1$, $R^2$ and Het are as previously defined, can be prepared from the nitrile of formula (F) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahyrofuran complex to provide an alcohol, tosylation of the alcohol with tosyl chloride in the presence of a base like pyridine to give a tosylate and replacement of the tosylate with the sodium salt of the desired thiol.

Scheme E

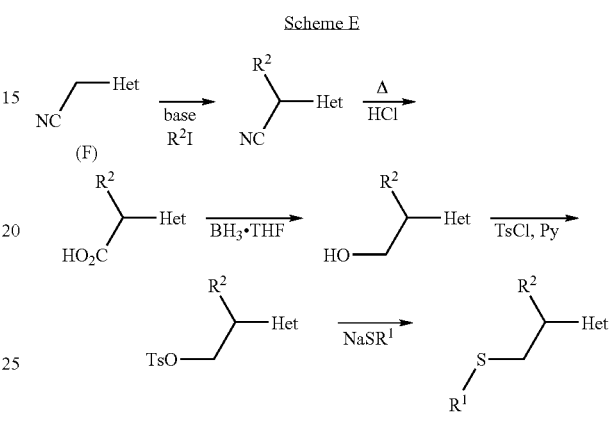

In Scheme F, the sulfide of formula ($A_4$), wherein n is 0, $R^1$ is —$CH_2$—, L is —$CH(CH_2)_p$— where p is either 2 or 3 and, taken together with $R^1$, S and L form a 5- or 6-membered ring, and Het is as previously described can be prepared from tetrahydrothiophene (p=2) or pentamethylene sulfide (p=3) (G). Chlorination of the cyclic sulfide starting material with N-chlorosuccinimide in benzene followed by alkylation with certain lithiated heterocycles or Grignard reagents can lead to the desired sulfides ($A_4$) in satisfactory yield.

Scheme F

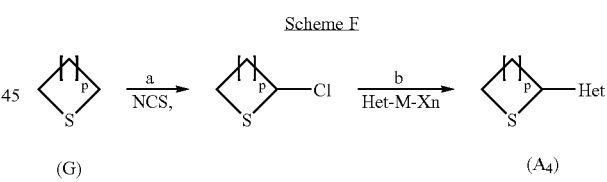

A more efficient protocol to access cyclic sulfides of formula ($A_4$) is illustrated in Scheme G where Het is a 6-substituted pyridin-3-yl and Z is previously defined. Accordingly, thiourea is added to a substituted chloromethyl pyridine, which, after hydrolysis, and alkylation with the appropriate bromo chloroalkane (p=1, 2, or 3) under aqueous base conditions, yields sulfide (H). Subsequent cyclization of (G) in the presence of a base like potassium-t-butoxide in a polar aprotic solvent such as THF provides cyclic sulfide ($A_4$).

Scheme G

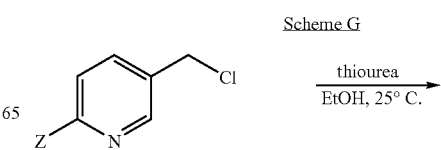

Scheme I

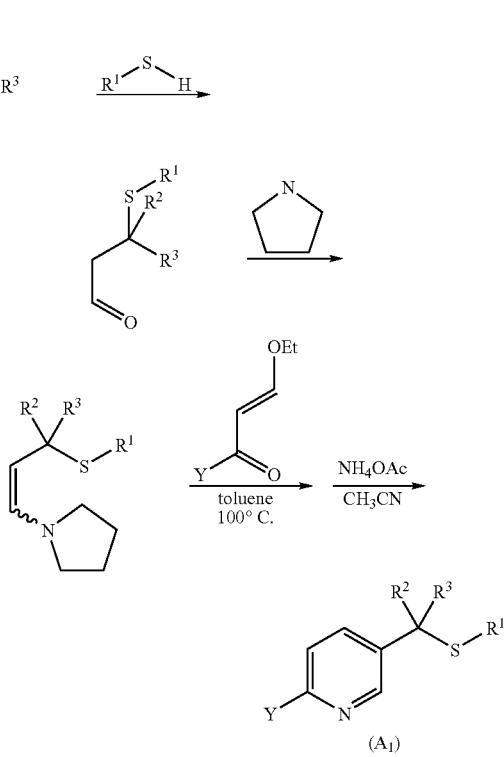

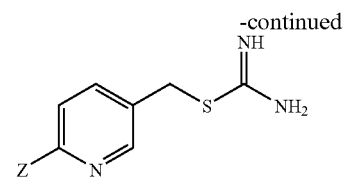

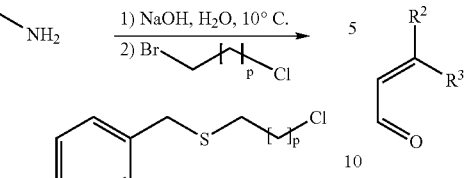

(H)

↓ KO'Bu
THF, HMPA, 25° C.

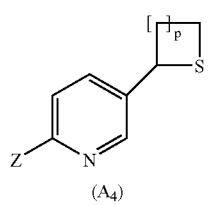

(A₄)
where p = 1, 2, or 3

Certain sulfides of formula (A₁) wherein Het is a substituted pyridin-3-yl, Z is as previously defined, and R¹, R²=CH₃ can be prepared alternatively via methods illustrated in Scheme H. Accordingly, the appropriate enone is coupled with dimethylaminoacrylonitrile and cyclized with ammonium acetate in DMF to yield the corresponding 6-substituted nicotinonitrile. Treatment with methyl-magnesium bromide, reduction with sodium borohydride, chlorination with thionyl chloride, and nucleophilic substitution with the sodium salt of an alkyl thiol provides desired sulfides (A₁).

Scheme H

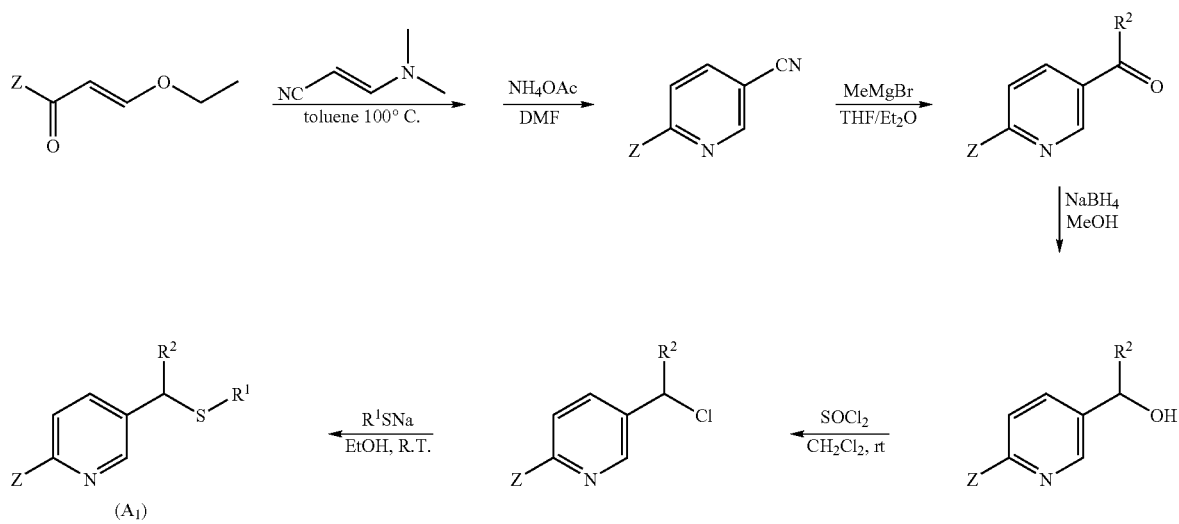

A variation of Scheme H is illustrated in Scheme I, wherein enamines, formed from the addition of an amine, e.g., pyrrolidine, with the Michael adduct of certain sulfides with appropriately substituted α,β-unsaturated aldehydes, are coupled with substituted enones and cyclized with ammonium acetate in CH₃CN to yield the desired sulfides (A₁) wherein R¹, R², R³, and Z are previously defined.

The oxidizing agents employed in the present invention are ruthenium tetraoxide or an alkali metal of permanganate.

Ruthenium tetraoxide is a powerful oxidant and is most conveniently generated in situ from an alkali metal periodate in the presence of a water soluble ruthenium salt capable of being converted to ruthenium tetraoxide. The water soluble ruthenium salt need only be present in a catalytic amount, generally from about 0.05 to about 2.0 mole percent based on the amount of sulfilimine. A stoichiometric amount of periodate is generally preferred but it is often convenient to employ from about 0.9 to about 1.1 molar equivalents based on the amount of sulfilimine. Ruthenium salts capable of being converted to ruthenium tetraoxide include, but are not limited to, ruthenium dioxide and ruthenium chloride with ruthenium chloride being preferred. Sodium and potassium periodate are the preferred alkali metal periodates.

Sodium and potassium permanganate are the preferred alkali metal permanganates with sodium permanganate being most preferred. The range of permanganate salt equivalents can be from about 0.9 to about 1.1 relative to the sulfilimine substrate. The preferred number of equivalents is about 0.95. When working up the permanganate reaction mixture it is advisable to quench the excess permanganate. Salts of meta-bisulfite (such as sodium or potassium) can be used in the quench step of the workup. The preferred salt of choice is sodium. The number of equivalents of meta-bisulfite can range from about 1.0 to about 5.0 relative to the permanganate stoichiometry. The preferred range of equivalents is from about 2.0 to about 4.0.

The process of the present invention is conducted in a suitable organic solvent that is essentially inert to the strong oxidizing conditions. Particularly suitable organic solvents are halogenated aliphatic and halogenated aromatic hydrocarbons such as dichloromethane, chloroform, 1,2-dichloroethane and dichlorobenzene, and aliphatic and aromatic nitriles such as acetonitrile and benzonitrile. The preferred reaction solvents are methylene chloride and acetonitrile. It is often convenient to perform the oxidation in a biphasic solvent system comprising a mixture of, for example, a halogenated aliphatic hydrocarbon such as dichloromethane and water.

The reaction temperature can range from about −10° C. to about 45° C. The preferred range is about 10° C. to about 30° C.

The sulfilimine substrate can be dissolved in the organic solvent and con-added to the aqueous solution of oxidizing agent or the solution of aqueous oxidizing agent can be added to the solution of sulfilimine in the organic solvent. The preferred addition order is con-adding the sulfilimine solution to the aqueous solution of the oxidizing agent.

The following examples are presented to illustrate the invention.

EXAMPLES

Example 1

Preparation of methyl-5-(2-chloro)pyridine-methyl-N-cyanosulfoximine.

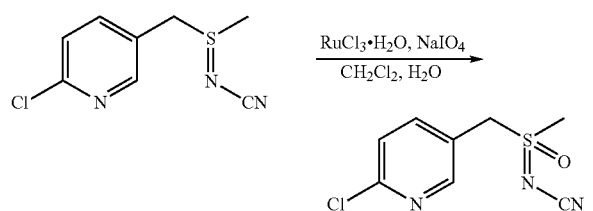

5-(2-chloro)pyridine-methyl-N-cyanosulfilimine (151 g, 0.7 mol) was dissolved in 4 liters of dichloromethane and added to a solution of sodium periodate (302 g, 1.4 mol) in 3 liters of water. Ruthenium(III) chloride hydrate (160 mg) was added and the mixture stirred for 20 minutes at room temperature. The organic phase was separated, dried over MgSO$_4$, treated with charcoal and then filtered and concentrated. The tan solid was triturated in a mixture of acetone and hexane, collected by filtration and dried to 110 g of product. mp 120-122° C. $^1$H NMR (300 MHz, CDCl$_3$) δ 8.5 (d, 1H, J=1.9), 7.9 (dd, 1H, J=1.9, 8.3), 7.6 (d, 1H, J=8.3), 5.1 (s, 2H), 3.45 (s, 3H).

Example 2

Preparation of methyl-5-(2-chloro)pyridine-1-ethyl-N-cyanosulfoximine.

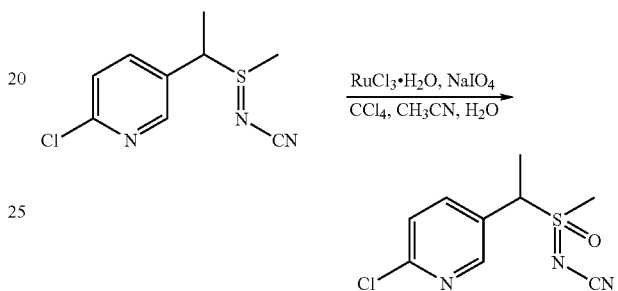

A solution of 300 grams of sodium periodate was prepared in 3.1 liters of water. 2 liters of carbon tetrachloride and 1.7 liters of acetonitrile was added to the solution followed by 1.6 grams of ruthenium(III) chloride hydrate. 5-(2-Chloro)pyridine-1-ethyl-N-cyanosulfilimine (161 g, 0.7 mol) was dissolved in 350 milliliters of acetonitrile and added to the stirred mixture at room temperature. After 20 minutes, the organic phase was separated, washed with aqueous NaHSO$_3$, dried over MgSO$_4$, treated with charcoal and then filtered and concentrated. The resulting solid was triturated in a mixture of hexane and acetone to give 101 g of a 3:2 mixture of diastereomers as a white solid. mp 102-110° C. $^1$H NMR (300 MHz, d$_6$-DMSO) δ 8.5 (d, 1H), 8.0 (m, 1H), 7.6 (d, 1H), 5.2 (m, 1H), 3.45 (m, 3H); 1.8 (d, 3H).

Example 3

Preparation of methyl-5-(2-chloro-3-nitro)pyridine-methyl-N-cyanosulfoximine.

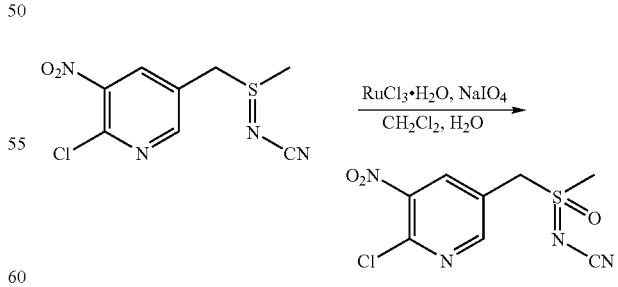

A solution was prepared by adding sodium periodate (661 mg, 3.1 mmol) to 7 milliliters of water at 25° C. followed by 7 milliliters of dichloromethane followed by ruthenium(III) chloride hydrate (8.7 mg, 0.04 mmol). 5-(2-Chloro-3-nitro) pyridine-methyl-N-cyanosulfilimine (400 mg, 1.5 mmol) was dissolved in 3 milliliters of dichloromethane and added dropwise to the solution at room temperature. After 20 minutes, the organic phase was separated, dried, filtered and concentrated. The residue was purified by column chromatography to give the product. mp 138-140° C. $^1$H NMR (400 MHz, CDCl$_3$/DMSO) δ 8.44 (d, 1H), 8.31 (d, 1H), 4.82 (s, 2H), 3.04 (s, 3H). LC-MS (ELSD): mass calculated for C$_8$H$_8$ClN$_4$O$_3$S [M+H]$^+$ 275. Found 275.

Example 4

Preparation of methyl-5-(2-chloro-3-methoxy)pyridine-methyl-N-cyanosulfoximine.

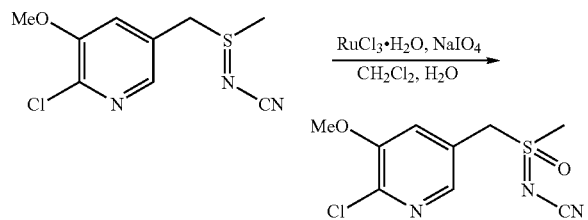

A solution was prepared by adding sodium periodate (351 mg, 1.6 mmol) to 3 milliliters of water at 25° C. followed by 3 milliliters of dichloromethane followed by ruthenium(III) chloride hydrate (4.6 mg, 0.021 mmol). 5-(2-Chloro-3-methoxy)pyridine-methyl-N-cyanosulfilimine (200 mg, 0.82 mmol) was dissolved in 2.5 milliliters of dichloromethane and added dropwise to the solution and stirred for 30 minutes at room temperature. The organic phase was separated after filtration, dried over Na$_2$SO$_4$, filtered and concentrated to a white solid. mp 123-125° C. $^1$H NMR (400 MHz, CDCl$_3$) δ 7.98 (d, 1H), 7.41 (d, 1H), 4.63 (dd, 1H), 3.99 (s, 3H), 3.11 (s, 3H). LC-MS (ELSD): mass calculated for C$_9$H$_{11}$ClN$_3$O$_2$S [M+H]$^+$ 260. Found 260.

Example 5

Preparation of methyl-5-(2-chloro-3-bromo)pyridine-methyl-N-cyanosulfoximine.

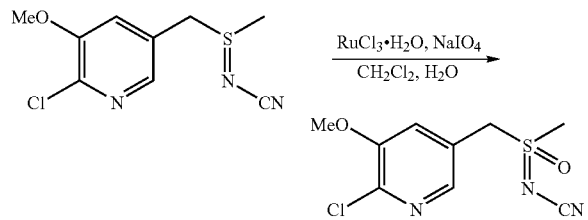

A solution was prepared by adding sodium periodate (246 mg, 1.2 mmol) to 3 milliliters of water at 25° C. followed by 3 milliliters of dichloromethane followed by ruthenium(III) chloride hydrate (6.6 mg, 0.029 mmol). 5-(2-Chloro-3-bromo)pyridine-methyl-N-cyanosulfilimine (170 mg, 0.6 mmol) was dissolved in 2 milliliters of dichloromethane and added dropwise to the solution and stirred 1 hour at room temperature. The organic phase was separated, dried over MgSO$_4$, filtered and concentrated to a white solid. mp 139-142° C. $^1$H NMR (400 MHz, CDCl$_3$/DMSO) δ 8.6 (d, 1H), 8.4 (d, 1H), 5.1 (s, 2H), 3.5 (s, 3H). LC-MS (ELSD): mass calculated for C$_8$H$_7$BrClN$_3$OS [M+H]$^+$ 308. Found 308.

Example 6

Preparation of methyl-5-(2-methoxy)pyridine-methyl-N-cyanosulfoximine.

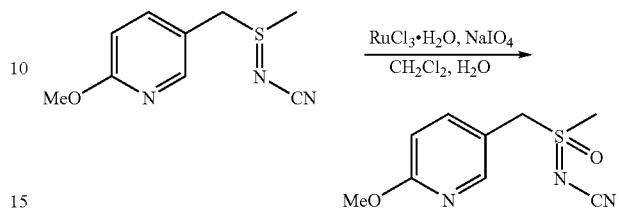

A solution was prepared by adding sodium periodate (818 mg, 3.8 mmol) to 6 milliliters of water at 25° C. followed by 6 milliliters of dichloromethane followed by Ruthenium(III) chloride hydrate (22 mg, 0.095 mmol). 5-(2-methoxy)pyridine-methyl-N-cyanosulfilimine (400 mg, 1.9 mmol) was dissolved in 3 milliliters of dichloromethane and added dropwise to the solution. The reaction was diluted with CH$_2$Cl$_2$ (10 milliliters) and passed through a diatomaceous earth plug. The organic phase was separated, dried over MgSO$_4$, filtered and concentrated to furnish the sulfoximine as a yellow solid. mp=89-91° C. $^1$H NMR (400 MHz, CDCl$_3$/DMSO) δ 8.2 (d, 1H), 7.7 (dd, 1H), 6.9 (d, 1H), 4.5 (s, 2H), 4.0 (s, 3H), 3.1 (s, 3H). LC-MS (ELSD): mass calculated for C$_9$H$_{11}$N$_3$O$_2$S [M+H]$^+$ 225. Found 225.

Example 7

Preparation of 3-[5-(2-trifluoromethyl)pyridine]-N-cyano-cyclopentylsulfoximine.

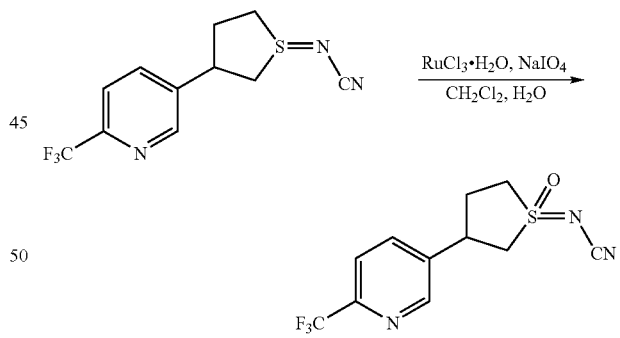

A solution was prepared by adding sodium periodate (861 mg, 4.07 mmol) to 14 milliliters of water followed by 24 milliliters of dichloromethane followed by ruthenium(III) chloride hydrate (8 mg, 0.04 mmol). 3-[5-(2-Trifluoromethyl)-pyridine-N-cyano-cyclopentylsulfilimine (1.00 mg, 3.66 mmol) was added to the solution. The solution was stirred overnight at room temperature. Isopropyl alcohol (0.5 milliliters) was added to the solution. The reaction was passed through a diatomaceous earth pad. The organic phase was separated, dried over MgSO$_4$, filtered and concentrated to furnish the sulfoximine as a off-white solid (360 mg, 34%). $^1$H NMR (400 MHz, acetone-d$_6$) δ 8.89 (overlapping doublets, 1H), 8.25 (m, 1H), 7.9 (overlapping doublets, 1H), 4.4-3.9 (m, 2H), 3.8-3.6 (m, 3H), 3.0-2.5 (m, 2H).

Example 8

Preparation of methyl-5-(2-trifluoromethyl)pyridine-1-ethyl-N-cyanosulfoximine.

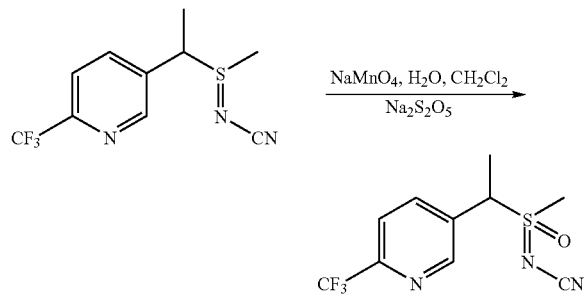

To a four neck 5 L round bottom flask fitted with an addition funnel, reflux condenser, mechanical stirring, and thermowell was charged with 1472 g (0.845 mol) of a 15% w/w of sulfilimine in dichloromethane. The solution was cooled to 3° C. in an ice-water bath with stirring. To this solution was added 299 g (0.845 mol) of a 40% w/w sodium permanganate aqueous solution dropwise via addition funnel over a 2 h period. The addition rate was controlled so that the internal temperature rose from 3° C. to 11° C. during the permanganate addition. The addition funnel was rinsed with 80 mL of water. The reaction was then allowed to stir with ice bath cooling for about 1 h. To this mixture was added a solution of 645 g of sodium metabisulfite (3.38 mol) in 1200 mL of water over a 1.5 h period. A definite exotherm was noted during the initial addition of the bisulfite solution (internal solution temp rose from 3° C. to 30° C.). An additional 250 mL of water was added and the reaction was allowed to stir an additional 2 h until all of brown manganese by-products were etched away from the reactor vessel walls. To this mixture was added 180 mL of acetonitrile. About 2 L of the reaction mixture was suction filtered through a coarse glass fritted funnel (filtration was fast), and the filter cake was washed with 250 mL of dichloromethane. The organic layer was then concentrated on a rotovap. The remaining portion of the reaction mixture was filtered through the same fritted funnel and the filter cake was washed with another 250 mL of dichloromethane. The bottom organic layer was collected and added to the other portion and concentrated on a rotovap to give 228 g (97% yield based on theortical) of an off-white solid. LC assay of this crude material indicated that the purity was about 96%.

Example 9

Preparation of methyl-5-(2-trifluoromethyl)pyridine-1-ethyl-N-cyanosulfoximine.

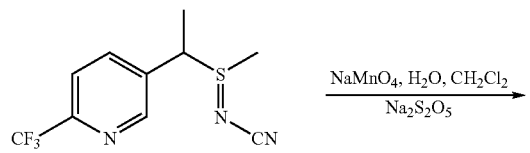

-continued

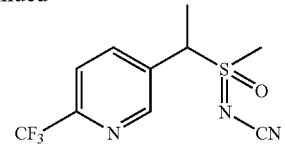

In a 5 L 4-neck round bottom flask, a mixture of 400 mL of dichloromethane, 400 mL of water, and 320 mL (1.25 mol) of a 40% aq solution of NaMnO$_4$ was cooled to 13° C. with an ice-bath. To this rapidly stirred mixture was added dropwise a solution of (~1.0 mol) sulfilimine in 1000 mL of dichloromethane (~1560 g) over 1¾ h. During this time the ice-bath was lowered or raised to maintain a reaction temperature of 13-20° C. After stirring for 30 min at 15° C., a solution of 570 g (3.0 mol, 3 equiv) of sodium metabisulfite in 900 mL of water was added with rapid stirring over 1.5 h. Very exothermic, the temperature rose from 15-28° C. rapidly at first. The mixture was stirred at RT (23° C.) for 30 min, and then filtered. The solid was rinsed with two wet cake volumes of dichloromethane. The clear two phase mixture was transferred to a 4 L separatory funnel, and the bottom organics collected. The aqueous layer was reextracted with 30 mL of dichloromethane, and the organics combined with the first cut. The solution was concentrated in vacuo to give 275 g of a white solid. This solid was air-dried overnight in a hood to give 260 g and finally in a vacuum oven at 40° C. to give 259 g (93% wt) of a white solid. LC analysis indicated a 30:68 (area) ratio of two isomers and a 97% area purity.

Example 10

Preparation of methyl-5-(2-trifluoromethyl)pyridine-1-ethyl-N-cyanosulfoximine.

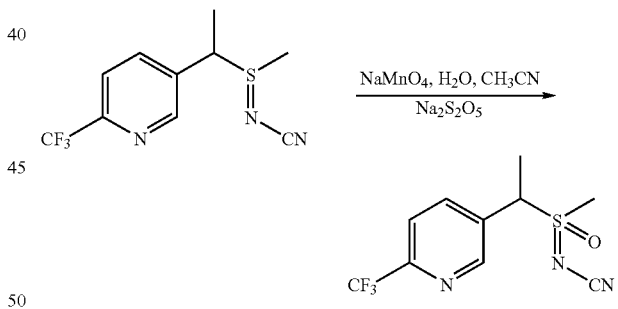

A solution of sulfilimine (~0.022 moles) in acetonitrile (50 mL) was cooled in an ice bath to about 5° C. To the well stirred solution was added (8.0 grams, 0.022 moles) of a 40 weight % aqueous solution of NaMnO$_4$ over about 20 minutes. During the addition the reaction temperature increased to about 24° C. The resulting brown reaction slurry was allowed to stir for about 30 minutes and then cooled to about 5° C. A 30 weight % aqueous solution of sodium metabisulfite (29.8 grams, 0.047 moles) was added to the vigorously stirred reaction mixture in portions during about 20 minutes. The addition is exothermic, the temperature increasing by 15 to 20° C. during the course of the addition. The reaction mixture slurry thickened during the addition. Additional acetonitrile (5 mL) and water (5 mL) were added to facilitate mixing. The quenched reaction mixture was vacuum filtered through a medium sintered glass filter funnel. The collected grey solids were rinsed with acetonitrile (5 mL). The combined filtrate and wash was transferred to a separatory funnel, the phases were allowed to separate and the lower aqueous phase removed. The upper organic phase was concentrated in vacuo, with an isopropyl alcohol solvent chase (40 grams) to afford 5.2 grams (83% weight recovery) of crude sulfoximine as a yellow solid. Recrystallization from isopropyl alcohol (4 mL) gave 3.3 grams (52%) of sulfoximine as a white solid. LC analysis indicated a 81:19 (area) ratio of the two isomers and a 89% area purity.

What is claimed is:

1. A process for the preparation of insecticidal sulfoximines (Ia),

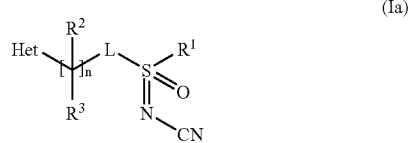

wherein
Het represents:

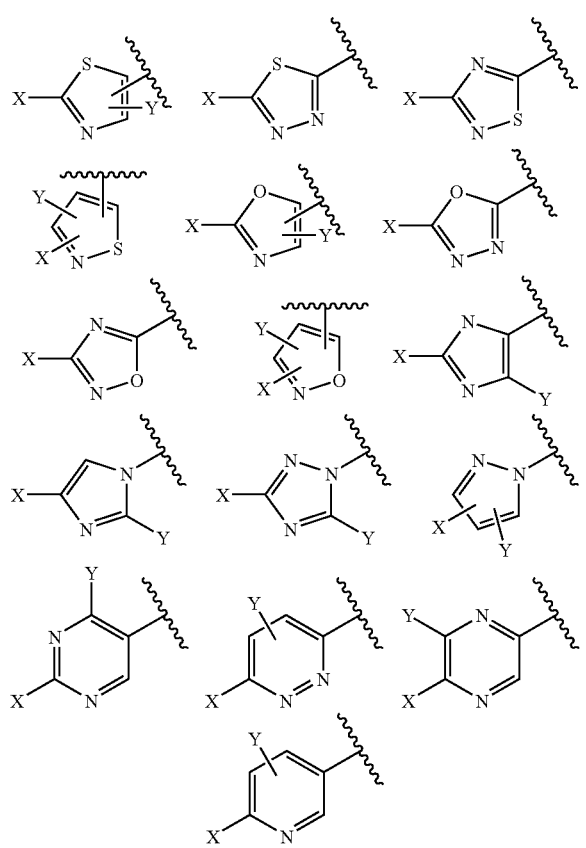

X represents halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $SO_mR^6$ where m is an integer from 0-2, $COOR^4$ or $CONR^4R^5$;

Y represents hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalk-enyl, $C_1$-$C_4$ alkoxy, $C_1$-$C_4$ haloalkoxy, CN, $NO_2$, $SO_mR^1$ where m is an integer from 0-2, $COOR^4$, $CONR^4R^5$, aryl or heteroaryl;

n is an integer from 0-3;

L represents either a single bond, —CH(CH$_2$)$_p$— where $R^1$, S and L taken together represent a 4-, 5-, or 6-membered ring and p is an integer from 1-3, —CH (CH$_2$OCH$_2$)— where $R^1$, S and L taken together represent a 6-membered ring, or —CH— where L, $R^2$ and the common carbon to which they connect taken together represent a 4-, 5-, or 6-membered ring with up to, but no more than, 1 heteroatom;

$R^1$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl, heteroarylalkyl, or —CH$_2$— in cases where $R^1$, S and L taken together represent a 4-, 5-, or 6-membered ring;

$R^2$ and $R^3$ independently represent hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $SO_mR^6$ where m is an integer from 0-2, $COOR^4$, $CONR^4R^5$, arylalkyl, heteroarylalkyl, or $R^2$ and $R^3$ and the common carbon to which they attach form a 3-6 membered ring;

$R^4$ and $R^5$ independently represent hydrogen, $C_1$-$C_4$ alkyl, $C_1$-$C_4$ haloalkyl; $C_3$-$C_6$ alkenyl, $C_3$-$C_6$ alkynyl, $C_3$-$C_6$ haloakenyl, aryl, heteroaryl, arylalkyl or heteroarylalkyl; and $R^6$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl or heteroarylalkyl;

which comprises oxidizing a sulfilimine of formula (I)

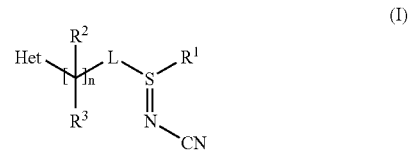

wherein
$R^1$, $R^2$, $R^3$, L, Het and n are as previously defined
by contacting the sulfilimine in a suitable organic solvent that is essentially inert to the strong oxidizing conditions with an oxidizing agent comprising ruthenium tetraoxide or an alkali metal permanganate at a temperature from about –10 to about 45° C.

2. The process of claim 1 in which Het is (6-substituted) pyridin-3-yl or (2-substituted)thiazol-5-yl and where X is halogen or $C_1$-$C_2$ haloalkyl and Y is hydrogen.

3. The process of claim 1 in which the starting sulfilimine has the structure

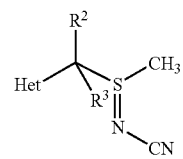

wherein
Het, $R^2$ and $R^3$ are as previously defined, $R^1$ is methyl, n is 1, and L is a single bond.

4. The process of claim 1 in which the starting sulfilimine has the structure

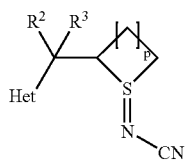

wherein
n is 1, $R^1$, S and L taken together form a standard 4-, 5-, or 6-membered ring such that L is —CH(CH$_2$)$_p$— and p is an integer from 1-3, and $R^1$ is —CH$_2$— and Het, $R^2$ and $R^3$ are as previously defined.

5. The process of claim 1 in which the starting sulfilimine has the structure

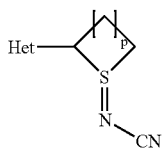

wherein
n is 0, $R^1$, S and L taken together form a standard 4-, 5-, or 6-membered ring such that L is —CH(CH$_2$)$_p$— and p is an integer from 1-3, and $R^1$ is —CH$_2$— and Het is as previously defined.

6. The process of claim 1 in which the temperature is from about 10° C. to about 30° C.

7. The process of claim 1 in which the oxidizing agent is an alkali metal permanganate.

8. The process of claim 1 in which the oxidizing agent is ruthenium tetraoxide.

9. The process of claim 8 in which the ruthenium tetraoxide is generated in situ from an alkali metal periodate in the presence of a water soluble ruthenium salt capable of being converted to ruthenium tetraoxide.

10. The process of claim 9 in which the water soluble ruthenium salt capable of being converted to ruthenium tetraoxide is ruthenium chloride.

11. The process of claim 1 in which the organic solvent is a halogenated aliphatic or halogenated aromatic hydrocarbon or an aliphatic or aromatic nitrile.

12. The process of claim 1 in which the process is conducted in a biphasic solvent system comprising a mixture a halogenated aliphatic hydrocarbon and water.

* * * * *